United States Patent
Bergmann

(10) Patent No.: US 10,793,626 B2
(45) Date of Patent: Oct. 6, 2020

(54) ADRENOMEDULLIN BINDER FOR USE IN THERAPY OF CANCER

(71) Applicant: ANGIOBIOMED GMBH, Hennigsdorf (DE)

(72) Inventor: Andreas Bergmann, Berlin (DE)

(73) Assignee: ANGIOBIOMED GMBH, Hennigsdorf (DE)

( * ) Notice: Subject to any disclaimer, the term of this patent is extended or adjusted under 35 U.S.C. 154(b) by 0 days.

(21) Appl. No.: 15/105,712

(22) PCT Filed: Dec. 19, 2014

(86) PCT No.: PCT/EP2014/078870
§ 371 (c)(1),
(2) Date: Jun. 17, 2016

(87) PCT Pub. No.: WO2015/092021
PCT Pub. Date: Jun. 25, 2015

(65) Prior Publication Data
US 2016/0319007 A1    Nov. 3, 2016

(30) Foreign Application Priority Data

Dec. 20, 2013   (EP) ................................. 13199000

(51) Int. Cl.
| | | |
|---|---|---|
| C07K 16/22 | (2006.01) | |
| C07K 16/26 | (2006.01) | |
| A61K 39/395 | (2006.01) | |
| A61K 9/00 | (2006.01) | |
| A61K 45/06 | (2006.01) | |
| C07K 16/30 | (2006.01) | |
| A61K 39/00 | (2006.01) | |

(52) U.S. Cl.
CPC ............ *C07K 16/22* (2013.01); *A61K 9/0019* (2013.01); *A61K 39/395* (2013.01); *A61K 39/39558* (2013.01); *A61K 45/06* (2013.01); *C07K 16/26* (2013.01); *C07K 16/30* (2013.01); *A61K 2039/505* (2013.01); *C07K 2317/34* (2013.01); *C07K 2317/92* (2013.01)

(58) Field of Classification Search
None
See application file for complete search history.

(56) References Cited

U.S. PATENT DOCUMENTS

2005/0175619 A1* 8/2005 Duffy ................. A61K 47/6875
424/178.1
2007/0248604 A1* 10/2007 Desnoyers ............ C07K 16/22
424/136.1

FOREIGN PATENT DOCUMENTS

| WO | 97/07214 A1 | 2/1997 | |
|---|---|---|---|
| WO | WO 97/07214 | * 2/1997 | ............ C12N 15/16 |

OTHER PUBLICATIONS

Mariuzza (Annu. Rev. Biophys. Biophys. Chem., 16: 139-159, 1987).*
Miller et al. (Journal of Biological Chemistry, 271(38): 23345-23351, 1996).*
International Search Report dated Mar. 25, 2015, issued in corresponding PCT/EP2014/078870, 6 pages.
Miller, M. J. et al., "Adrenomedullin expression in human tumor cell lines: Its potential role as an autocrine growth factor", Journal of Biological Chemistry, American Society for Biochemistry and Molecular Biology, vol. 271, No. 38, XP002184272, Sep. 1, 1996, pp. 23345-23351.
Nouguerede, E. et al., "Expression of adrenomedullin in human colorectal tumors and its role in cell growth and invasion in vitro and in xenograft growth in vivo", Cancer Medicine, vol. 2, No. 2, XP055110951, Apr. 29, 2013, pp. 196-207.
Ouafik, L. et al., "Neutralization of adrenomedullin inhibits the growth of human glioblastoma cell lines in vitro and suppresses tumor xenograft growth in vivo", The American Journal of Pathology, vol. 160, No. 4, XP002421261, 2002, pp. 1279-1292.
Berenguer-Daize, C. et al., "Adrenomedullin blockade suppresses growth of human hormone-independent prostate tumor xenograft in mice", Clinical cancer research, The American Association for Cancer Research, vol. 19, No. 22, XP008168601, Nov. 14, 2013, pp. 6138-6150.
Martinez, A. et al., "The Effects of Adrenomedullin Overexpression in Breast Tumor Cells", Journal of the National Cancer Institute, XP055110963, Aug. 21, 2002, pp. 1226-1237.

* cited by examiner

*Primary Examiner* — Nelson B Moseley, II
(74) *Attorney, Agent, or Firm* — Millen, White, Zelano & Branigan, PC; Ryan Pool

(57) ABSTRACT

Subject matter of the present invention is an anti-ADM antibody or anti-ADM antibody fragment or anti-ADM non-Ig scaffold binding to the C-terminal portion of ADM, the aa 43-52 of ADM (SEQ ID NO: 1): APRSKISPQGY-NH2 for use in a therapy of cancer. Subject matter of the present invention is anti-ADM antibody or anti-ADM antibody fragment or anti-ADM non-Ig scaffold for use in the treatment of cancer according to claim 1 wherein said anti-ADM antibody or anti-ADM antibody fragment or anti-ADM non-Ig scaffold requires the presence of a C-terminally amidated tyrosine residue within the C-terminal portion of ADM, the aa 43-52 of ADM (SEQ ID NO: 1): APRSKISPQGY-NH2, for binding.

11 Claims, 1 Drawing Sheet
Specification includes a Sequence Listing.

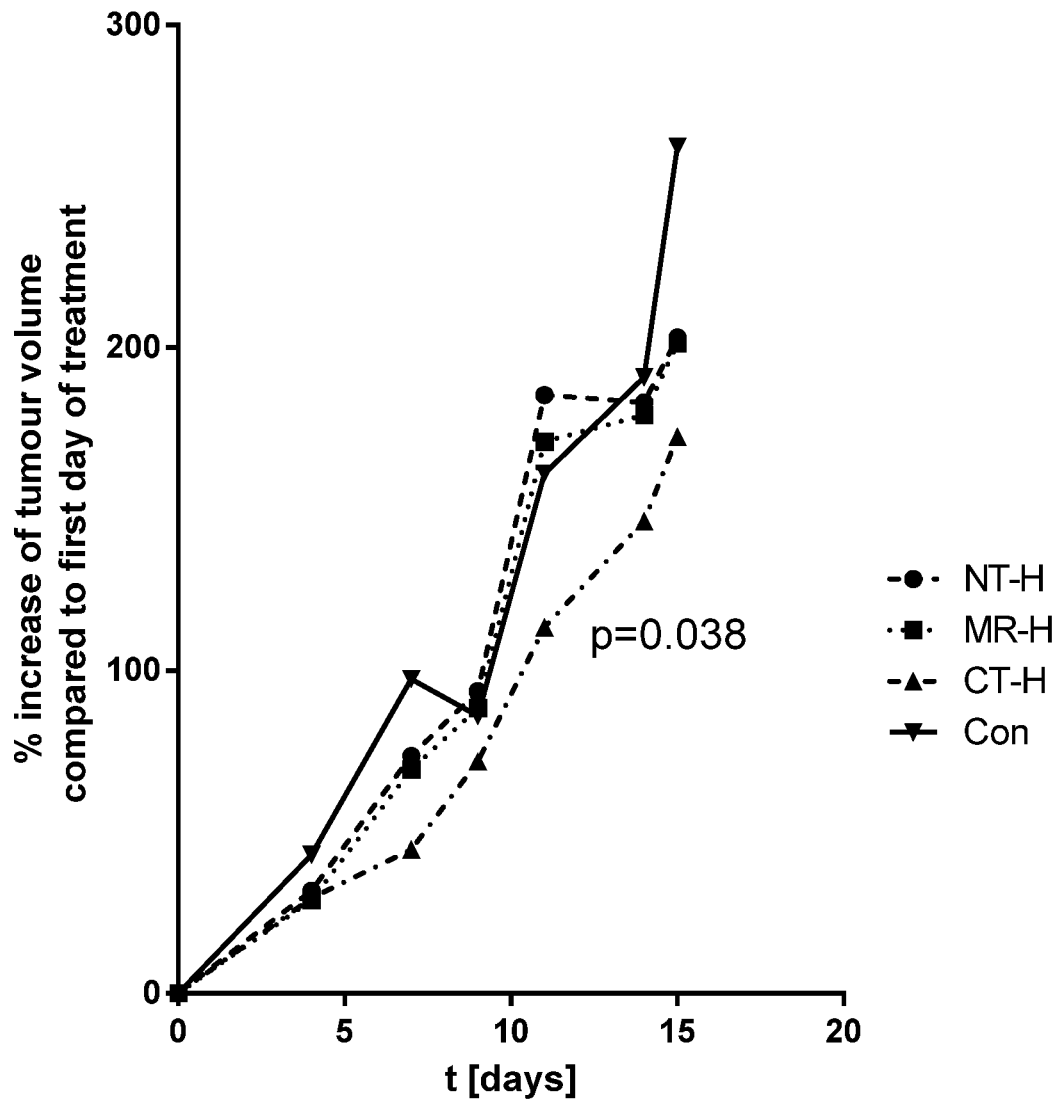

SEQUENCE LISTING

<160> NUMBER OF SEQ ID NOS: 14

<210> SEQ ID NO 1
<211> LENGTH: 13
<212> TYPE: PRT
<213> ORGANISM: Homo sapiens

<400> SEQUENCE: 1

Ala Pro Arg Ser Lys Ile Ser Pro Gln Gly Tyr Asn His
1               5                   10

<210> SEQ ID NO 2
<211> LENGTH: 52
<212> TYPE: PRT
<213> ORGANISM: Homo sapiens

<400> SEQUENCE: 2

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 3
<211> LENGTH: 31
<212> TYPE: PRT
<213> ORGANISM: Homo sapiens

<400> SEQUENCE: 3

Thr Val Gln Lys Leu Ala His Gln Ile Tyr Gln Phe Thr Asp Lys Asp
1               5                   10                  15

Lys Asp Asn Val Ala Pro Arg Ser Lys Ile Ser Pro Gln Gly Tyr
            20                  25                  30

<210> SEQ ID NO 4
<211> LENGTH: 20
<212> TYPE: PRT
<213> ORGANISM: Homo sapiens

<400> SEQUENCE: 4

Phe Thr Asp Lys Asp Lys Asp Asn Val Ala Pro Arg Ser Lys Ile Ser
1               5                   10                  15

Pro Gln Gly Tyr
            20

<210> SEQ ID NO 5
<211> LENGTH: 21
<212> TYPE: PRT
<213> ORGANISM: Homo sapiens

<400> SEQUENCE: 5

Phe Thr Asp Lys Asp Lys Asp Asn Val Ala Pro Arg Ser Lys Ile Ser
1               5                   10                  15

Pro Gln Gly Tyr Gly
            20

<210> SEQ ID NO 6
<211> LENGTH: 19
<212> TYPE: PRT

<213> ORGANISM: Homo sapiens

<400> SEQUENCE: 6

Phe Thr Asp Lys Asp Lys Asp Asn Val Ala Pro Arg Ser Lys Ile Ser
1               5                   10                  15

Pro Gln Gly

<210> SEQ ID NO 7
<211> LENGTH: 18
<212> TYPE: PRT
<213> ORGANISM: Homo sapiens

<400> SEQUENCE: 7

Phe Thr Asp Lys Asp Lys Asp Asn Val Ala Pro Arg Ser Lys Ile Ser
1               5                   10                  15

Pro Gln

<210> SEQ ID NO 8
<211> LENGTH: 17
<212> TYPE: PRT
<213> ORGANISM: Homo sapiens

<400> SEQUENCE: 8

Phe Thr Asp Lys Asp Lys Asp Asn Val Ala Pro Arg Ser Lys Ile Ser
1               5                   10                  15

Pro

<210> SEQ ID NO 9
<211> LENGTH: 16
<212> TYPE: PRT
<213> ORGANISM: Homo sapiens

<400> SEQUENCE: 9

Phe Thr Asp Lys Asp Lys Asp Asn Val Ala Pro Arg Ser Lys Ile Ser
1               5                   10                  15

<210> SEQ ID NO 10
<211> LENGTH: 15
<212> TYPE: PRT
<213> ORGANISM: Homo sapiens

<400> SEQUENCE: 10

Phe Thr Asp Lys Asp Lys Asp Asn Val Ala Pro Arg Ser Lys Ile
1               5                   10                  15

<210> SEQ ID NO 11
<211> LENGTH: 14
<212> TYPE: PRT
<213> ORGANISM: Homo sapiens

<400> SEQUENCE: 11

Phe Thr Asp Lys Asp Lys Asp Asn Val Ala Pro Arg Ser Lys
1               5                   10

<210> SEQ ID NO 12
<211> LENGTH: 21
<212> TYPE: PRT
<213> ORGANISM: Homo sapiens

<400> SEQUENCE: 12

Tyr Arg Gln Ser Met Asn Asn Phe Gln Gly Leu Arg Ser Phe Gly Cys
1               5                   10                  15

```
Arg Phe Gly Thr Cys
            20

<210> SEQ ID NO 13
<211> LENGTH: 12
<212> TYPE: PRT
<213> ORGANISM: Homo sapiens

<400> SEQUENCE: 13

Cys Thr Val Gln Lys Leu Ala His Gln Ile Tyr Gln
1               5                   10

<210> SEQ ID NO 14
<211> LENGTH: 12
<212> TYPE: PRT
<213> ORGANISM: Homo sapiens

<400> SEQUENCE: 14

Cys Ala Pro Arg Ser Lys Ile Ser Pro Gln Gly Tyr
1               5                   10
```

ADRENOMEDULLIN BINDER FOR USE IN THERAPY OF CANCER

Subject matter of the present invention is an anti-ADM antibody or anti-ADM antibody fragment or anti-ADM non-Ig scaffold binding to the C-terminal portion of ADM, the aa 43-52 of ADM (SEQ ID NO: 1): APRSKISPQGY-NH2 for use in a therapy of cancer.

Subject matter of the present invention is in one embodiment an anti-ADM antibody or anti-ADM antibody fragment or anti-ADM non-Ig scaffold for use in the treatment of cancer according to claim 1 wherein said anti-ADM antibody or anti-ADM antibody fragment or anti-ADM non-Ig scaffold requires the presence of a C-terminally amidated tyrosine residue within the C-terminal portion of ADM, the aa 43-52 of ADM (SEQ ID NO: 1): APRSKISPQGY-NH2, for binding.

The peptide adrenomedullin (ADM) was described for the first time in 1993 (Kitamura, K., et al., "Adrenomedullin: A Novel Hypotensive Peptide Isolated From Human Pheochromocytoma", Biochemical and Biophysical Research Communications, Vol. 192 (2), pp. 553-560 (1993)) as a novel hypotensive peptide comprising 52 amino acids, which had been isolated from a human pheochromocytome; (SEQ ID No.: 2). In the same year, cDNA coding for a precursor peptide comprising 185 amino acids and the complete amino acid sequence of this precursor peptide were also described. The precursor peptide, which comprises, inter alia, a signal sequence of 21 amino acids at the N-terminus, is referred to as "preproadrenomedullin" (pre-proADM). In the present description, all amino acid positions specified usually relate to the pre-proADM which comprises the 185 amino acids. The peptide adrenomedullin (ADM) is a peptide which comprises 52 amino acids (SEQ ID NO: 2) and which comprises the amino acids 95 to 146 of pre-proADM, from which it is formed by proteolytic cleavage. To date, substantially only a few fragments of the peptide fragments formed in the cleavage of the pre-proADM have been more exactly characterized, in particular the physiologically active peptides adrenomedullin (ADM) and "PAMP", a peptide comprising 20 amino acids (22-41) which follows the 21 amino acids of the signal peptide in pre-proADM. The discovery and characterization of ADM in 1993 triggered intensive research activity, the results of which have been summarized in various review articles, in the context of the present description, reference being made in particular to the articles to be found in an issue of "Peptides" devoted to ADM in particular (Editorial, Takahashi, K., "Adrenomedullin: from a pheochromocytoma to the eyes", Peptides, Vol. 22, p. 1691 (2001)) and (Eto, T., "A review of the biological properties and clinical implications of adrenomedullin and proadrenomedullin N-terminal 20 peptide (PAMP), hypotensive and vasodilating peptides", Peptides, Vol. 22, pp. 1693-1711 (2001)). A further review is (Hinson, et al., "Adrenomedullin, a Multifunctional Regulatory Peptide", Endocrine Reviews, Vol. 21(2), pp. 138-167 (2000)). In the scientific investigations to date, it has been found, inter alia, that ADM may be regarded as a polyfunctional regulatory peptide. It is released into the circulation in an inactive form extended by glycine (Kitamura, K., et al., "The intermediate form of glycine-extended adrenomedullin is the major circulating molecular form in human plasma", Biochem. Biophys. Res. Commun., Vol. 244(2), pp. 551-555 (1998). Abstract Only). There is also a binding protein (Pio, R., et al., "Complement Factor H is a Serum-binding Protein for adrenomedullin, and the Resulting Complex Modulates the Bioactivities of Both Partners", The Journal of Biological Chemistry, Vol. 276(15), pp. 12292-12300 (2001)) which is specific for ADM and probably likewise modulates the effect of ADM. Those physiological effects of ADM as well as of PAMP which are of primary importance in the investigations to date were the effects influencing blood pressure.

Hence, ADM is an effective vasodilator, and thus it is possible to associate the hypotensive effect with the particular peptide segments in the C-terminal part of ADM. It has furthermore been found that the above-mentioned further physiologically active peptide PAMP formed from pre-proADM likewise exhibits a hypotensive effect, even if it appears to have an action mechanism differing from that of ADM (cf. in addition to the abovementioned review articles (Eto, T., "A review of the biological properties and clinical implications of adrenomedullin and proadrenomedullin N-terminal 20 peptide (PAMP), hypotensive and vasodilating peptides", Peptides, Vol. 22, pp. 1693-1711 (2001)) and (Hinson, et al., "Adrenomedullin, a Multifunctional Regulatory Peptide", Endocrine Reviews, Vol. 21(2), pp. 138-167 (2000)) also (Kuwasako, K., et al., "Purification and characterization of PAMP-12 (PAMP-20) in porcine adrenal medulla as a major endogenous biologically active peptide", FEBS Lett, Vol. 414(1), pp. 105-110 (1997). Abstract only), (Kuwasaki, K., et al., "Increased plasma proadrenomedullin N-terminal 20 peptide in patients with essential hypertension", Ann. Clin. Biochem., Vol. 36 (Pt. 5), pp. 622-628 (1999). Abstract only) or (Tsuruda, T., et al., "Secretion of proadrenomedullin N-terminal20 peptide from cultured neonatal rat cardiac cells", Life Sci., Vol. 69(2), pp. 239-245 (2001). Abstract only) and EP-A2 0 622 458). It has furthermore been found that the concentrations of ADM which can be measured in the circulation and other biological liquids are, in a number of pathological states, significantly above the concentrations to be found in healthy control persons. Thus, the ADM level in patients with congestive heart failure, myocardial infarction, kidney diseases, hypertensive disorders, Diabetes mellitus, in the acute phase of shock and in sepsis and septic shock are significantly increased, although to different extents. The PAMP concentrations are also increased in some of said pathological states, but the plasma levels are lower relative to ADM ((Eto, T., "A review of the biological properties and clinical implications of adrenomedullin and proadrenomedullin N-terminal 20 peptide (PAMP), hypotensive and vasodilating peptides", Peptides, Vol. 22, pp. 1693-1711 (2001)); page 1702). It is furthermore known that unusually high concentrations of ADM are to be observed in sepsis, and the highest concentrations in septic shock (cf. (Eto, T., "A review of the biological properties and clinical implications of adrenomedullin and proadrenomedullin N-terminal 20 peptide (PAMP), hypotensive and vasodilating peptides", Peptides, Vol. 22, pp. 1693-1711 (2001)) and (Hirata, et al., "Increased Circulating Adrenomedullin, a Novel Vasodilatory Peptide, in Sepsis", Journal of Clinical Endocrinology and Metabolism, Vol. 81(4), pp. 1449-1453 (1996)), (Ehlenz, K., et al., "High levels of circulating adrenomedullin in severe illness: Correlation with C-reactive protein and evidence against the adrenal medulla as site of origin", Exp Clin Endocrinol Diabetes, Vol. 105, pp. 156-162 (1997)), (Tomoda, Y., et al., "Regulation of adrenomedullin secretion from cultured cells", Peptides, Vol. 22, pp. 1783-1794 (2001)), (Ueda, S., et al., "Increased Plasma Levels of Adrenomedullin in Patients with Systemic Inflammatory Response Syndrome", Am. J. Respir. Crit. Care Med., Vol. 160, pp. 132-136 (1999)) and (Wang, P., "Adrenomedullin and cardiovascular responses in sepsis", Peptides, Vol. 22, pp. 1835-1840 (2001)).

Known in the art is further a method for identifying adrenomedullin immunoreactivity in biological liquids for diagnostic purposes and, in particular within the scope of sepsis diagnosis, cardiac diagnosis and cancer diagnosis. According to WO2004/090546, the midregional partial peptide of the proadrenomedullin, which contains amino acids (45-92) of the entire preproadrenomedullin, is measured, in particular, with an immunoassay which works with at least one labeled antibody that specifically recognizes a sequence of the mid-proADM (WO2004/090546).

WO-A1 2004/097423 describes the use of an antibody against adrenomedullin for diagnosis, prognosis, and treatment of cardiovascular disorders. Treatment of diseases by blocking the ADM receptor are also described in the art, (e.g. WO-A1 2006/027147, PCT/EP2005/012844) said diseases may be sepsis, septic shock, cardiovascular diseases, infections, dermatological diseases, endocrinological diseases, metabolic diseases, gastroenterological diseases, cancer, inflammation, hematological diseases, respiratory diseases, muscle skeleton diseases, neurological diseases, urological diseases.

Several possibilities have been described to modulate the ADM signaling system to suppress tumor cell growth, including the use of peptide (ADM 22-52) [1] and small molecule ADM receptor antagonists [2], as well as antibodies directed against either the ADM receptor [3] or ADM [4]. In more detail, the use of anti-ADM antibodies has been described as follows: It has been described that neutralization of Adrenomedullin with polyclonal anti-ADM 1-52 antibodies inhibits the growth of human glioblastoma cell lines in vitro and suppresses tumor xenograft growth in vivo [5]. The antibodies used displayed full reactivity only against full length ADM 1-52, whereas it was markedly reduced against N-terminally truncated ADM peptide variants.

A monoclonal anti-ADM antibody (MoAb-G6) was shown to suppress growth of several tumor cell lines (NCI-H157, NCI-H720, MCF-7, NIH:OVCAR-3) by 30-50%, when applied at 100 μg/mL [6]. MoAb-G6 is an IgA-type antibody developed by immunization with peptidePreproADM 116-146 (T-V-Q-K-L-A-H-Q-I-Y-Q-F-T-D-K-D-K-D-N-V-A-P-R-S-K-I-S-P-Q-G-Y-NH2 (SEQ ID No: 3)) (also termed PO72) [7]. The precise epitope of monoclonal antibody MoAb-G6 is not known.

The monoclonal antibody MoAb-G6 was said to neutralize ADM bioactivity (U.S. Pat. No. 7,939,639) and it was shown to completely inhibit ADM binding to its receptor. WO/2006/027147 describes approaches to treat cancer with binders (including antibodies) to the ADM receptor.

Subject matter of the present invention is an anti-ADM antibody or anti-ADM antibody fragment or anti-ADM non-Ig scaffold binding to the C-terminal portion of ADM, the aa 43-52 of ADM (SEQ ID NO: 1): APRSKISPQGY-NH2 for use in a therapy of cancer.

The anti-ADM antibody or anti-ADM antibody fragment or anti-ADM non-Ig scaffold binding to the C-terminal portion of ADM, the aa 43-52 of ADM (SEQ ID NO: 1): APRSKISPQGY-NH2 exhibits favorable properties in comparison to known antibodies when treating cancer. The anti-ADM antibody or anti-ADM antibody fragment or anti-ADM non-Ig scaffold binding to the C-terminal portion of ADM, the aa 43-52 of ADM (SEQ ID NO: 1): APRSKISPQGY-NH2 has an enhanced ability to reduce tumour growth significantly in comparison to known ADM antibodies.

Such an antibody may be selected from the group comprising: CT-H, CT-H-1, CT-H-2, CT-H3, CT-H-Gly, CT-H-OH (Tabelle3) which are described as followed:

Antibodies from group CT-H, CT-H-1, CT-H-2, CT-H-3 are defined as an anti-ADM antibody or anti-ADM antibody fragment or anti-ADM non-Ig scaffold binding to the C-terminal portion of ADM, the aa 43-52 of ADM (SEQ ID NO: 1) and binds to biotin-FTDKDKDNVAPRSKISPQGY-NH2 (SEQ ID NO: 4) and binds under comparable conditions to biotin-FTDKDKDNVAPRSKISPQGYG-OH (SEQ ID NO: 5) less than 20%, preferably less than 10%, more preferably less than 5%, and most preferably less than 1% compared to the binding to biotin-FTDKDKDNVAPR-SKISPQGY-NH2 (SEQ ID NO: 4).

Antibody CT-H-Gly is defined as an anti-ADM antibody or anti-ADM antibody fragment or anti-ADM non-Ig scaffold binding to the C-terminal portion of ADM, the aa 43-52 of ADM (SEQ ID NO: 1) and binds to biotin-FTDKDKDNVAPRSKISPQGY-NH2 (SEQ ID NO: 4), and binds under comparable conditions to biotin-FTDKDKDNVAPRSKISPQGYG-OH (SEQ ID NO: 5) more than 100%, preferably more than 200%, more preferably more than 300%, and most preferably more than 400% compared to the binding to biotin-FTDKDKDNVAPRSKISPQGY-NH2 (SEQ ID NO: 4).

Antibody CT-H-OH is defined as an anti-ADM antibody or anti-ADM antibody fragment or anti-ADM non-Ig scaffold binding to the C-terminal portion of ADM, the aa 43-52 of ADM (SEQ ID NO: 1) and binds to biotin-FTDKDKDNVAPRSKISPQGY-NH2 (SEQ ID NO: 4) and binds under comparable conditions to biotin-FTDKDKDNVAPRSKISPQGY-OH (SEQ ID NO: 4) more than 500%, preferably more than 1000%, more preferably more than 1500%, and most preferably more than 2500% compared to the binding to biotin-FTDKDKDNVAPRSKISPQGY-NH2 (SEQ ID NO: . . . ).

ADM throughout the specification means adrenomedullin. Throughout the specification the "antibodies", or "antibody fragments" or "non-Ig scaffolds" in accordance with the invention are capable to bind ADM, and thus are directed against ADM, and thus can be referred to as "anti-ADM antibodies", "anti-ADM antibody fragments", or "anti-ADM non-Ig scaffolds".

In another embodiment of the invention the anti-ADM antibodies, anti-ADM antibody fragments, or anti-ADM non-Ig scaffolds provided by the invention are capable to bind circulating ADM, and thus are directed against circulating ADM.

Anti-adrenomedullin (ADM) antibody is an antibody that binds specifically to ADM, anti-adrenomedullin antibody fragment is a fragment of an ADM antibody wherein said fragment binds specifically to ADM. An anti-ADM non-Ig scaffold is a non-Ig scaffold that binds specifically to ADM. Specifically binding to ADM allows binding to other antigens as well. This means, this specificity would not exclude that the antibody may cross-react with other polypeptides than that against it has been raised. This also pertains the specificity of the anti-ADM antibody fragment, or anti-ADM non-Ig scaffold in accordance with the invention.

Subject matter of the present invention is in one embodiment anti-ADM antibody or anti-ADM antibody fragment or anti-ADM non-Ig scaffold is for use in the treatment of cancer wherein said anti-ADM antibody or anti-ADM antibody fragment or anti-ADM non-Ig scaffold requires the presence of a C-terminally amidated tyrosine residue within the C-terminal portion of ADM, the aa 43-52 of ADM (SEQ ID NO: 1): APRSKISPQGY-NH2, for binding.

An antibody, which requires the presence of a C-terminally amidated tyrosine residue within the C-terminal portion of ADM, the aa 43-52 of ADM (SEQ ID NO: 1): APRSKISPQGY-NH2, for binding is defined as follows: It is an antibody, which binds to biotin-FTDKDKDNVAPR-SKISPQGY-NH2 (SEQ ID NO: 4), and binds under comparable conditions to biotin-FTDKDKDNVAPRSKISPQ-GYG-OH (SEQ ID NO: 5) less than 20%, preferably less than 10%, more preferably less than 5%, and most preferably less than 1% compared to the binding to biotin-FTDKDKDNVAPRSKISPQGY-NH2 (SEQ ID NO: 4).

In other words, subject matter of the present invention is in one embodiment an anti-ADM antibody or anti-ADM antibody fragment or anti-ADM non-Ig scaffold for use in the treatment of cancer wherein said anti-ADM antibody or anti-ADM antibody fragment or anti-ADM non-Ig scaffold binds to a C-terminally amidated tyrosine residue within the C-terminal portion of ADM, the aa 43-52 of ADM (SEQ ID NO: 1): APRSKISPQGY-NH2 and binds under comparable conditions to biotin-FTDKDKDNVAPRSKISPQGYG-OH (SEQ ID NO: 5) less than 20%, preferably less than 10%, more preferably less than 5%, and most preferably less than 1% compared to the binding to biotin-FTDKDKDNVAPR-SKISPQGY-NH2 (SEQ ID NO: 4). Comparable conditions mean the use of the same binding assay such an assay is described in Example 1.

An antibody that requires the presence of a C-terminally amidated tyrosine residue at the C-terminal portion of ADM can be developed by immunization with an antigen containing a C-terminal portion of ADM including the free C-terminal amidated tyrosine residue of ADM (position 52 of ADM). After such immunization an antibody that requires the presence of a C-terminally amidated tyrosine residue at the C-terminal portion of ADM can be selected from this immunization process by testing its binding to the C-terminal portion of ADM including the free C-terminal amidated tyrosine residue of ADM (position 52 of ADM) and to related peptides (in case of development of monoclonal antibodies secreted from respective hybridoma cell lines would be tested): Such antibody must bind to the C-terminal portion of ADM including the free C-terminal amidated tyrosine, but not to the C-terminal portion of ADM containing the C-terminal tyrosine residue (position 52 of ADM), which C-terminally has a COOH-group instead of an amide group. It also must not bind to the C-terminal portion of ADM devoid of at least the C-terminal tyrosine residue (position 52 of ADM).

It has been described that plasma concentrations of the C-terminally amidated, biologically active Adrenomedullin is about 5-fold smaller than of the C-terminally glycine-extended, biologically inactive Adrenomedullin variant (1 Kitamura K, Kato J, Kawamoto M, Tanaka M, Chino N, Kangawa K, Eto T. The intermediate form of glycine-extended adrenomedullin is the major circulating molecular form in human plasma. Biochemical and biophysical research communications 1998; 244:551-5.). Consequently, an antibody, which specifically binds to the C-terminally amidated, biologically active Adrenomedullin, but essentially not to the C-terminally glycine-extended, biologically inactive Adrenomedullin variant can be applied at least at an about 5-fold smaller dose compared to an antibody without this differential binding specificity to achieve the same binding of the C-terminally amidated, biologically active Adrenomedullin in vivo. Moreover, an antibody without binding specificity for the amidated C-terminus might also bind to pro- or pre-pro-Adrenomedullin and be consumed by this binding at an unpredictable high rate. Thus, and antibody with binding specificity for the amidated C-terminus is expected to be applicable at an even far more than 5-fold smaller dose compared to an antibody without this differential binding specificity to achieve the same binding of the C-terminally amidated, biologically active Adrenomedullin in vivo. Applying a therapeutic compound at a smaller dose is associated with less side effects and is also more cost effective.

ADM is expressed in a variety of tumors where it aggravates several of the molecular and physiological features of malignant cells. ADM has been shown to be a mitogenic factor stimulating growth in several cancer types and to encourage a more aggressive tumor phenotype. In addition, ADM is an apoptosis survival factor for cancer cells and an indirect suppressor of the immune response. ADM plays an important role in environments subjected to low oxygen tensions, which is a typical feature in the proximity of solid tumors. Under these conditions, ADM is upregulated through a hypoxia-inducible factor 1 (HIF-1)-dependent pathway and acts as a potent angiogenic factor promoting neovascularization. [8, 9].

In a specific embodiment of the present invention said Anti-ADM antibody or anti-ADM antibody fragment or anti-ADM non-Ig scaffold is for use in the treatment of cancer wherein said cancer is selected from the group comprising: prostate, breast, colon, lung, bladder, skin, uterus, cervix, oral cavity and pharynx, stomach, ovaries, kidney, pancreas, non-Hodgekin-lymphome, leukemia, liver, esophagus, testicle, thyroid, central nervous system, larynx, gall bladder, plasmocytome, and morbus hodgekin.

In another specific embodiment of the present invention said Anti-ADM antibody or anti-ADM antibody fragment or anti-ADM non-Ig scaffold is for use in the treatment of cancer wherein said cancer is selected from the group comprising: prostate, breast, colon, lung, bladder, skin, uterus, cervix, kidney, pancreas, oral cavity and pharynx, stomach, and ovaries.

In a specific embodiment said cancer that is to be treated is a K-RAS positive cancer.

The RAS proteins are small GTPase enzymes that transmit signals within cells. They are critical to cells because of the central role they play in cell growth and survival. One of those genes, K-RAS, which was discovered nearly 30 years ago, is mutated in 30 percent of human tumors, including 90 percent of pancreatic cancers, 40 percent of colon cancers, and 20 percent of non-small cell lung cancers. Activating K-RAS mutations are the most frequent oncogenic mutations in human cancer. Cancers with K-RAS mutations are aggressive and respond poorly to standard therapies. The constitutive activation of K-RAS and persistent stimulation of downstream signalling pathways drive many of the hallmarks of cancer, sustained proliferation, metabolic reprogramming, anti-apoptosis, remodelling of the tumour microenvironment, evasion of the immune response, cell migration and metastasis (Pylayeva-Gupta et al, 2011). Pylayeva-Gupta Y, Grabocka E, Bar-Sagi D (2011) RAS oncogenes: weaving a tumorigenic web. Nat Rev Cancer 11: 761-774.

In clinical practice, K-RAS mutation defines a subset of patients for whom prognosis is generally poor and treatment options are limited. There are no drugs that target RAS proteins directly or indirectly and there are no therapies effective for RAS-driven cancers. Thus RAS and K_RAS cancers are excluded from treatment with targeted therapies.

A single amino acid substitution, and in particular a single nucleotide substitution in the K-Ras gene, is responsible for an activating mutation. Most KRAS mutations occur in codon 12 or 13 of the gene. A variety of laboratory methods have been developed to assess mutation status of the KRAS gene. Many of these methods, including allele-specific PCR, real-time PCR methods with melt-curve analysis, and nucleic acid sequencing techniques, provide the appropriate analytical performance to address tissue heterogeneity in tumor samples as described in Anderson SM Laboratory methods for KRAS mutation analysis. Expert Rev Mol Diagn. 2011 July; 11(6):635-42. The current gold standard for K-RAS testing remains direct sequencing of PCR amplification products (Nollau P, Wagener C: Methods for detection of point mutations: performance and quality assessment. IFCC Scientific Division, Committee on Molecular Biology Techniques. Clin Chem 1997, 43:1114-1128).

Adrenomedullin (ADM) was identified by Wang et al (2014) [Wang L, Gala M, Yamamoto M, Pino M S, Kikuchi H, Shue D S, Shirasawa S, Austin T R, Lynch M P, Rueda B R, Zukerberg L R, Chung D C: Adrenomedullin is a therapeutic target in colorectal cancer, Int. J. Cancer: 134, 2041-2050 (2014)] as one of the most significantly upregulated genes in human colon cancer cell lines that express the KRAS oncogene, particularly under hypoxic conditions as occur in solid tumors. In vivo knockdown of ADM by short hairpin RNAs (shRNA) directed to various coding regions of ADM in colon tumor xenografts blocked angiogenesis and stimulated apoptosis, resulting in tumor suppression. Among 56 patients with CRC, significantly higher expression levels of ADM were observed in samples harboring a KRAS mutation. It is suggested that mutant KRAS may play a specific role in tumor survival in hypoxic environments and acts synergistic to upregulate ADM. Collectively, the enhanced activation of ADM by mutant K-Ras may play a critical role in the adaptation of colon tumors to hypoxic stress conditions.

The anti-ADM antibody or anti-adrenomedullin antibody fragment or anti-ADM non-Ig scaffold according to the present invention exhibits an affinity towards human ADM in such that affinity constant is smaller than $10^{-7}$ M, preferred $10^{-8}$ M, preferred affinity constant is smaller than $10^{-9}$ M, most preferred smaller than $10^{-10}$ M. A person skilled in the art knows that it may be considered to compensate lower affinity by applying a higher dose of compounds and this measure would not lead out-of-the-scope of the invention. The affinity constants may be determined according to the method as described in Example 1.

An antibody according to the present invention is a protein including one or more polypeptides substantially encoded by immunoglobulin genes that specifically binds an antigen. The recognized immunoglobulin genes include the kappa, lambda, alpha (IgA), gamma ($IgG_1$, $IgG_2$, $IgG_3$, $IgG_4$), delta (IgD), epsilon (IgE) and mu (IgM) constant region genes, as well as the myriad immunoglobulin variable region genes. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the NH2-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and F(ab')$_2$, as well as bifunctional hybrid antibodies and single chains (e.g., Lanzavecchia et al., Eur. J. Immunol. 17:105, 1987; Huston et al., Proc. Natl. Acad. Sci. U.S.A., 85:5879-5883, 1988; Bird et al., Science 242:423-426, 1988; Hood et al., Immunology, Benjamin, N.Y., 2nd ed., 1984; Hunkapiller and Hood, Nature 323:15-16, 1986). An immunoglobulin light or heavy chain variable region includes a framework region interrupted by three hypervariable regions, also called complementarity determining regions (CDR's) (see, Sequences of Proteins of Immunological Interest, E. Kabat et al., U.S. Department of Health and Human Services, 1983). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al., PCT Publication No. WO92/001047; and Winter, PCT Publication No. WO92/20791), or selected from a human combinatorial monoclonal antibody library (see the Morphosys website). Human antibodies can also be prepared by using transgenic animals carrying a human immunoglobulin gene (for example, see Lonberg et al., PCT Publication No. WO93/12227; and Kucherlapati, PCT Publication No. WO91/10741).

Thus, the anti-ADM antibody may have the formats known in the art. Examples are human antibodies, monoclonal antibodies, humanized antibodies, chimeric antibodies, CDR-grafted antibodies. In a preferred embodiment antibodies according to the present invention are recombinantly produced antibodies as e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains,e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines and numerous others.

In a preferred embodiment the anti-ADM antibody format is selected from the group comprising Fv fragment, scFv fragment, Fab fragment, scFab fragment, F(ab)$_2$ fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is the scFab format.

In addition to anti-ADM antibodies other biopolymer scaffolds are well known in the art to complex a target molecule and have been used for the generation of highly target specific biopolymers. Examples are aptamers, spiegelmers, anticalins and conotoxins. Aptamers are oligonucleotide acids or peptide molecules that bind to a specific target molecule. A spiegelmer is a RNA-like molecule built from L-ribose units that bind to a specific target molecule. Anticalins are artificial proteins that bind to a specific target molecule. They are derived from human lipocalins which are a family of naturally binding proteins. Anticalins are being used in lieu of monoclonal antibodies, but are about eight times smaller with a size of about 180 amino acids and a mass of about 20 kDa (Gebauer M, Skerra A: Engineered protein scaffolds as next-generation antibody therapeutics. Current opinion in chemical biology 2009, 13(3):245-255; Wurch T, Pierre A, Depil S: Novel protein scaffolds as emerging therapeutic proteins: from discovery to clinical proof-of-concept. Trends in biotechnology 2012, 30(11): 575-582., Skerra A (June 2008). "Alternative binding proteins: anticalins—harnessing the structural plasticity of the lipocalin ligand pocket to engineer novel binding activities". FEBS J. 275 (11): 2677-83.)

Non-Ig scaffolds may be protein scaffolds or peptide scaffolds and may be used as antibody mimics as they are capable to bind to ligands or antigens. Non-Ig scaffolds may be selected from the group comprising tetranectin-based non-Ig scaffolds (e.g. described in US 2010/0028995), fibronectin scaffolds (e.g. described in EP 1266 025; lipocalin-based scaffolds ((e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microproteins preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and Kunitz domain based scaffolds (e.g. described in EP 1941867).

Furthermore, in one embodiment of the invention an anti-Adrenomedullin (ADM) antibody or an anti-adrenomedullin antibody fragment or an anti-ADM non-Ig scaffold is monospecific. Monospecific anti-Adrenomedullin (ADM) antibody or monospecific anti-adrenomedullin antibody fragment or monospecific anti-ADM non-Ig scaffold means that said antibody or antibody fragment or non-Ig scaffold binds to one specific region encompassing preferably at least 4, or at least 5 amino acids within the target ADM. Monospecific anti-Adrenomedullin (ADM) antibody or monospecific anti-adrenomedullin antibody fragment or monospecific anti-ADM non-Ig scaffold are anti-Adrenomedullin (ADM) antibodies or anti-adrenomedullin antibody fragments or anti-ADM non-Ig scaffolds that all have affinity for the same antigen In another special embodiment the anti-ADM antibody or the antibody fragment binding to ADM is a monospecific antibody. Monospecific means that said antibody or antibody fragment binds to one specific region encompassing preferably at least 4, or preferably at least 5 amino acids within the target ADM. Monospecific antibodies or fragments are antibodies or fragments that all have affinity for the same antigen. Monoclonal antibodies are monospecific, but monospecific antibodies may also be produced by other means than producing them from a common germ cell.

In a specific embodiment of the invention the antibody is a monoclonal antibody or a fragment thereof. In one embodiment of the invention the anti-ADM antibody or the anti-ADM antibody fragment is a human or humanized antibody or derived therefrom. In one specific embodiment one or more (murine) CDR's are grafted into a human antibody or antibody fragment.

In one preferred embodiment of the invention antibodies according to the present invention may be produced as follows:

Balb/c mice were immunized with 100 μg Peptide-BSA-Conjugate (see Table 1) at day 0 and 14 (emulsified in 100 μl complete Freund's adjuvant) and 50 μg at day 21 and 28 (in 100 μl incomplete Freund's adjuvant). Three days before the fusion experiment was performed, the animal received 50 μg of the conjugate dissolved in 100 μl saline, given as one intraperitoneal and one intra venous injection.

Splenocytes from the immunized mice and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primarily screened for antigen specific IgG antibodies three weeks after fusion. The criterion for selecting the CT-H antibody producing hybridoma cell line was a positive binding against peptide APRSKISPQGY-NH$_2$ (SEQ ID NO: 1), but a negative binding against peptide APRSKISPQGY-COOH (SEQ ID NO: 1).

The positive tested microcultures were transferred into 24-well plates for propagation. After retesting the selected cultures were cloned and recloned using the limiting-dilution technique and the isotypes were determined.

(Lane, R. D. "A short-duration polyethylene glycol fusiontechnique for increasing production of monoclonal antibody-secreting hybridomas", J. Immunol. Meth. 81: 223-228; (1985), Ziegler, B. et al. "Glutamate decarboxylase (GAD) is not detectable on the surface of rat islet cells examined by cytofluorometry and complement-dependent antibody-mediated cytotoxicity of monoclonal GAD antibodies", Horm. Metab. Res. 28: 11-15, (1996)).

Antibodies may be produced by means of phage display according to the following procedure: The human naïve antibody gene libraries HALT/8 were used for the isolation of recombinant single chain F-Variable domains (scFv) against adrenomedullin peptide. The antibody gene libraries were screened with a panning strategy comprising the use of peptides containing a biotin tag linked via two different spacers to the adrenomedullin peptide sequence. A mix of panning rounds using non-specifically bound antigen and streptavidin bound antigen were used to minimize background of non-specific binders. The eluted phages from the third round of panning have been used for the generation of monoclonal scFv expressing *E. coli* strains. Supernatant from the cultivation of these clonal strains has been directly used for an antigen ELISA testing. (see also Hust, M., Meyer, T., Voedisch, B., Rülker, T., Thie, H., El-Ghezal, A., Kirsch, M.I., Schütte, M., Helmsing, S., Meier, D., Schirrmann, T., Dübel, S., 2011. A human scFv antibody generation pipeline for proteome research. Journal of Biotechnology 152, 159-170; Schütte, M., Thullier, P., Pelat, T., Wezler, X., Rosenstock, P., Hinz, D., Kirsch, M. I., Hasenberg, M., Frank, R., Schirrmann, T., Gunzer, M., Hust, M., Dübel, S., 2009. Identification of a putative Crf splice variant and generation of recombinant antibodies for the specific detection of *Aspergillus fumigatus*. PloS One 4, e6625)

Humanization of murine antibodies may be conducted according to the following procedure: For humanization of an antibody of murine origin the antibody sequence is modelling for the structural interaction of framework regions (FR) with the complementary determining regions (CDR) and the antigen. Based on structural modelling an appropriate FR of human origin is selected and the murine CDR sequences are transplanted into the human FR. Variations in the amino acid sequence of the CDRs or FRs may be introduced to regain structural interactions, which were abolished by the species switch for the FR sequences. This recovery of structural interactions may be achieved by random approach using phage display libraries or via directed approach guided by molecular modelling. (Almagro J C, Fransson J., 2008. Humanization of antibodies. Front Biosci. 2008 Jan. 1; 13:1619-33.)

In a preferred embodiment the ADM antibody format is selected from the group comprising Fv fragment, scFv fragment, Fab fragment, scFab fragment, F(ab)$_2$ fragment and scFv-Fc Fusion protein. In another preferred embodiment the antibody format is selected from the group comprising scFab fragment, Fab fragment, scFv fragment and bioavailability optimized conjugates thereof, such as PEGylated fragments.

One of the most preferred formats is a humanized antibody

In another preferred embodiment, the anti-ADM antibody, anti-ADM antibody fragment, or anti-ADM non-Ig scaffold is a full length antibody, antibody fragment, or non-Ig scaffold.

In a preferred embodiment the anti-adrenomedullin antibody or an anti-adrenomedullin antibody fragment or anti-adrenomedullin non-Ig scaffold is directed to and can bind to an epitope of at least 5 amino acids in length contained in ADM.

In a specific embodiment the anti-adrenomedullin antibody or an anti-adrenomedullin antibody fragment or anti-adrenomedullin non-Ig scaffold is directed to and can bind to an epitope of at least 4 amino acids in length contained in ADM.

In one specific embodiment said anti-ADM antibody or anti-ADM antibody fragment or anti-ADM non-Ig scaffold is for use in the treatment of cancer, wherein said antibody or fragment or scaffold is not ADM-binding-Protein-1 (complement factor H).

In one specific embodiment said anti-ADM antibody or anti-ADM antibody fragment or anti-ADM non-Ig scaffold is for use in the treatment of cancer, wherein said antibody or antibody fragment or non-Ig scaffold binds to a region of at least 4 or at least 5 amino acids within the sequence of aa 43-52 of ADM (SEQ ID NO: 1): APRSKISPQGY-NH2.

In one specific embodiment said anti-ADM antibody or anti-ADM antibody fragment or anti-ADM non-Ig scaffold is for use in the treatment of cancer, to be used in combination with other cancer medicaments. In one specific embodiment said anti-ADM antibody or anti-ADM antibody fragment or anti-ADM non-Ig scaffold is for use in the treatment of cancer, to be used in combination with Zytostatika, CD inhibitors, EGFR inhibitors, VEGFR inhibitors, TNFR inhibitors or Tyrosine kinase inhibitors. In another embodiment said anti-ADM antibody or anti-ADM antibody fragment or anti-ADM non-Ig scaffold is to be used as mono-therapeuticum.

Zytostatika are chemotherapeutic agents and known to the person skilled in the art and may may be selected from the group comprising the following:

Abirateron, Afatinib, Alitretinoin, Anastrozol, Bazedoxifen, Bevacizumab, Bicalutamid, Bleomycin, Capecitabin, Carboplatin, Cetuximab, Cisplatin, Clomifen, Crizotinib, Cyclophosphamid, Cyproteron, Dabrafenib, Dacarbazin, Dasatinib, Docetaxel, Doxorubicin, Enzalutamid, Epirubicin, Eribulin, Erlotinib, Etoposid, Exemestan, Filgrastim, Fludarabin, Fluorouracil, Fulvestrant, Gefitinib, Gemcitabin, Hydroxycarbamid, Ifosfamid, Imatinib, Ipilimumab, Irinotecan, Lapatinib, Lenalidomid, Letrozol, Methotrexat, Mitomycin, Nilotinib, Obinutuzumab, Ofatumumab, Oxaliplatin, Paclitaxel, Panitumumab, Permetrexed, Pertuzumab, Pomalidomid, Ponatinib, Raloxifen, Regorafenib, Tamoxifen, Temozolomid, Trastuzumab, Vemurafenib, Vinblastin, Vinflunin, Vinorelbin, Vismodegib.

In one embodiment said anti-ADM antibody or anti-ADM antibody fragment or anti-ADM non-Ig scaffold is for use in the treatment of cancer, to be used in combination with CD inhibitors wherein said CD inhibitors are selected from the group comprising Afutuzumab, Alemtuzumab, Bivatuzumab mertansine, Blinatumomab, Brentuximab vedotin, Dacetuzumab, Epratuzumab, Galiximab, Gemtuzumab ozogamicin, Ibritumomab tiuxetan, Inotuzumab ozogamicin, Intetumumab, Iratumumab, Lintuzumab, Lorvotuzumab mertansine, Lucatumumab, Lumiliximab, Milatuzumab, Moxetumomab pasudotox, Ocaratuzumab, Ofatumumab, Rituximab, Samalizumab, Taplitumomab paptox, Teprotumumab, Tositumomab (Bexxar), Veltuzumab and Vorsetuzumab mafodotin.

In one embodiment said anti-ADM antibody or anti-ADM antibody fragment or anti-ADM non-Ig scaffold is for use in the treatment of cancer, to be used in combination with EGFR inhibitors wherein said EGFR inhibitors are selected from the group comprising Cetuximab, Ertumaxomab, Imgatuzumab, Matuzumab, Necitumumab, Nimotuzumab, Panitumumab Patritumab, Pertuzumab, Trastuzumab, Zalutumumab and Zatuximab In one embodiment said anti-ADM antibody or anti-ADM antibody fragment or anti-ADM non-Ig scaffold is for use in the treatment of cancer, to be used in combination with VEGFR inhibitors wherein said VEGFR inhibitors are selected from the group comprising Alacizumab pegol, Icrucumab and Ramucirumab.

In one embodiment said anti-ADM antibody or anti-ADM antibody fragment or anti-ADM non-Ig scaffold is for use in the treatment of cancer, wherein said TNFR inhibitors are selected from the group comprising Conatumumab, Lexatumumab, Mapatumumab and Tigatuzumab.

In one specific embodiment said anti-ADM antibody or anti-ADM antibody fragment or anti-ADM non-Ig scaffold is for use in the treatment of cancer, to be used in combination with an agent selected from the group comprising Brentuximab vedotin, Cetuximab, Gemtuzumab ozogamicin, Ibritumomab tiuxetan, Ofatumumab, Panitumumab, Pertuzumab, Rituximab, Tositumomab (Bexxar) and Trastuzumab In another preferred embodiment said anti-ADM antibody or anti-ADM antibody fragment or anti-ADM non-Ig scaffold is for use in the treatment of cancer, to be used in combination with an agent selected from the group comprising Alemtuzumab, Bevacizumab, Brentuximab, Catumaxomab, Cetuximab, Ibritumomab-Tiuxetan, Ofatumumab, Panitumumab, Rituximab, Trastuzumab.

Subject matter of the present invention is a pharmaceutical composition comprising an Anti-ADM antibody or anti-ADM antibody fragment or anti-ADM non-Ig scaffold according to the invention, i.e. according to the hereinmentioned embodiments. Subject matter of the present invention is said pharmaceutical composition to be used as monotherapy.

Subject matter of the present invention is in one embodiment a pharmaceutical composition for use in the treatment of cancer to be used in combination with Zytostatika, CD inhibitors, EGFR inhibitors, VEGFR inhibitors, TNFR inhibitors or Tyrosine kinase inhibitors.

Zytostatika, CD inhibitors, EGFR inhibitors, VEGFR inhibitors, TNFR inhibitors or Tyrosine kinase inhibitors may be selected from those as disclosed above.

In one embodiment subject matter of the present invention is a pharmaceutical composition for use in the treatment of cancer, to be used in combination with: Alemtuzumab, Bevacizumab, Brentuximab, Catumaxomab, Cetuximab, Ibritumomab-Tiuxetan, Ofatumumab, Panitumumab, Rituximab, Trastuzumab.

Subject matter of the present invention in one embodiment is a pharmaceutical composition as described above for use in the treatment of cancer, wherein said pharmaceutical composition can be administered for instance intravenously.

Subject matter of the present invention is a method of treating cancer wherein a therapeutically effective amount said anti-ADM antibody or anti-ADM antibody fragment or anti-ADM non-Ig scaffold is administered to patient in need thereof. Said anti-ADM antibody or anti-ADM antibody fragment or anti-ADM non-Ig scaffold may be administered with or without any other anti-cancer agents as mentioned above. Subject matter of the present invention is a method of treating cancer wherein a therapeutically effective amount said pharmaceutical composition comprising said anti-ADM antibody or anti-ADM antibody fragment or anti-ADM non-Ig scaffold is administered to patient in need thereof. Said pharmaceutical composition may comprise other anti-cancer agents as mentioned above.

Said anti-ADM antibody or anti-ADM antibody fragment or anti-ADM non-Ig scaffold is administered at a dose, which results in molar excess over the concentration of circulating ADM. This can be in a range of 0.1-10 mg/kg. To maintain the desired concentration range over time, the application can be repeated in intervals which are depending on the in vivo half life time of it. These intervals can be between 2 and 7 days. Said anti-ADM antibody or anti-ADM antibody fragment or anti-ADM non-Ig scaffold are preferably formulated as saline-based solution and are preferably applied as a bolus injection or infusion intravenously. Conceptually, cancer patients overexpressing ADM and/or ADM receptor in their tumor are expected to benefit most from treatment with said anti-ADM antibody or anti-ADM antibody fragment or anti-ADM non-Ig scaffold. Thus, patients can be stratified by determining the expression level of ADM and/or ADM receptor out of tumor biopsies.

FIG. 1

Increase of tumour volume over time dependent on treatment with compounds. Compounds investigated were NT-H (monoclonal antibody raised against the N-terminal moiety of human Adrenomedullin), MR-H (monoclonal antibody raised against the midregional moiety of human Adrenomedullin), CT-H (monoclonal antibody raised against the C-terminal moiety of human Adrenomedullin) and Con (unspecific control antibody). Reduction of tumour growth was significant for CT-H ($p=0.038$); for NT-H and MR-H there was a trend for efficacy, but the effect was not statistically significant.

EXAMPLES

Example 1

Generation and Characterization of Antibodies

Several monoclonal antibodies against different moieties of Adrenomedullin were produced and their affinity constants were determined.

The antibodies were generated according to the following method: Balb/c mice were immunized with 100 µg Peptide-BSA-Conjugate (see Table 1) at day 0 and 14 (emulsified in 100 µl complete Freund's adjuvant) and 50 µg at day 21 and 28 (in 100 µl incomplete Freund's adjuvant). Three days before the fusion experiment was performed, the animal received 50 µg of the conjugate dissolved in 100 µl saline, given as one intraperitoneal and one intra venous injection.

Splenocytes from the immunized mice and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primarily screened for antigen specific IgG antibodies three weeks after fusion. The criterion for selecting the CT-H antibody producing hybridoma cell line was a positive binding against peptide APRSKISPQGY-NH$_2$ (SEQ ID NO: 1), but a negative binding against peptide APRSKISPQGY-COOH (SEQ ID NO: 1).

The positive tested microcultures were transferred into 24-well plates for propagation. After retesting the selected cultures were cloned and recloned using the limiting-dilution technique and the isotypes were determined.

(Lane, R. D. "A short-duration polyethylene glycol fusiontechnique for increasing production of monoclonal antibody-secreting hybridomas", J. Immunol. Meth. 81: 223-228; (1985), Ziegler, B. et al. "Glutamate decarboxylase (GAD) is not detectable on the surface of rat islet cells examined by cytofluorometry and complement-dependent antibody-mediated cytotoxicity of monoclonal GAD antibodies", Horm. Metab. Res. 28: 11-15, (1996)).

Monoclonal Antibody Production:

Antibodies were produced via standard antibody production methods (Marx et al, Monoclonal Antibody Production, ATLA 25, 121, 1997,) and purified via Protein A. The antibody purities were >95% based on SDS gel electrophoresis analysis.

Affinity Constants

To determine the affinity of the antibodies to Adrenomedullin, the kinetics of binding of Adrenomedullin to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare). (Lorenz et al., "Functional Antibodies Targeting IsaA of *Staphylococcus aureus* Augment Host Immune Response and Open New Perspectives for Antibacterial Therapy"; Antimicrob Agents Chemother. 2011 January; 55(1): 165-173.)

The monoclonal antibodies were raised against the below depicted regions of human ADM. The following table 1 represents a selection of obtained antibodies used in further experiments.

TABLE 1

Adrenomedullin-related Antigens/Immunogens and antibodies developed against these.

| Antigen/Immunogen | ADM Region | Designation of antibody | Affinity constants Kd (M) |
|---|---|---|---|
| YRQSMNNFQGLRSFGCRFGTC (SEQ ID NO: 12) | 1-21 | NT-H | $5.9 \times 10^{-8}$ |
| CTVQKLAHQIYQ (SEQ ID NO: 13) | 21-32 | MR-H | $2 \times 10^{-9}$ |
| CAPRSKISPQGY-NH$_2$ (SEQ ID NO: 14) | C-42-52 | CT-H | $1.1 \times 10^{-9}$ |

Epitope Mapping of Antibody CT-H

Several peptides related to the C-terminal region of ADM were synthesized (table 2).

TABLE 2

Epitop Mapping of CT-H: Adrenomedullin-related peptides are shown. Binding of CT-H to each peptide is expressed as percentage of binding observed in comparison to binding obtained against peptide P 33-52 NH2.

| Peptide # | Amino acid sequence | Position within ADM | Binding of CT-H [Bx/B P 33-52 NH2] |
|---|---|---|---|
| P 33-52 + G | Biotin-FTDKDKDNVAPRSKISPQGYG-OH (SEQ ID NO: 5) | 33-52 + G | 0.09% |

TABLE 2-continued

Epitop Mapping of CT-H: Adrenomedullin-related peptides are shown. Binding of CT-H to each peptide is expressed as percentage of binding observed in comparison to binding obtained against peptide P 33-52 NH2.

| Peptide # | Amino acid sequence | Position within ADM | Binding of CT-H [Bx/B P 33-52 NH2] |
|---|---|---|---|
| P 33-52 COOH | Biotin-FTDKDKDNVAPRSKISPQGY-OH (SEQ ID NO: 4) | 33-52 | 0.03% |
| P 33-52 NH2 | Biotin-FTDKDKDNVAPRSKISPQGY-NH2 (SEQ ID NO: 4) | 33-52 | 100.00% |
| P 33-51 | Biotin-FTDKDKDNVAPRSKISPQG-OH (SEQ ID NO: 6) | 33-51 | 0.02% |
| P 33-50 | Biotin-FTDKDKDNVAPRSKISPQ-OH (SEQ ID NO: 7) | 33-50 | 0.02% |
| P 33-49 | Biotin-FTDKDKDNVAPRSKISP-OH (SEQ ID NO: 8) | 33-49 | 0.02% |
| P 33-48 | Biotin-FTDKDKDNVAPRSKIS-OH (SEQ ID NO: 9) | 33-48 | 0.02% |
| P 33-47 | Biotin-FTDKDKDNVAPRSKI-OH (SEQ ID NO: 10) | 33-47 | 0.02% |
| P 33-46 | Biotin-FTDKDKDNVAPRSK-OH (SEQ ID NO: 11) | 33-46 | 0.02% |

Labelling Procedure:

100 ug (100 ul) of antibody CT-H (1 mg/ml in PBS, pH 7.4,) was mixed with 10 ul Akridinium NHS-ester (1 mg/ml in acetonitrile, InVent GmbH, Germany) and incubated for 20 min at room temperature. Labelled CT-H was purified by Gel-filtration HPLC on Bio-Sil® SEC 400-5 (Bio-Rad Laboratories, Inc., USA) The purified labeled antibody was diluted in (300 mmol/L potassiumphosphate, 100 mmol/L NaCl, 10 mmol/L Na-EDTA, 5 g/L Bovine Serum Albumin, pH 7.0). The final concentration was approx. 800.000 relative light units (RLU) of labelled antibody (approx. 20 ng labeled antibody) per 300 µL. Akridiniumester chemiluminescence was measured by using an AutoLumat LB 953 (Berthold Technologies GmbH & Co. KG).

Solid Phase:

Polystyrene tubes (Greiner Bio-One International AG, Austria) were coated (18 h at room temperature) with Streptavidin (1.5 µg/0.3 mL 100 mmol/L NaCl, 50 mmol/L TRIS/HCl, pH 7.8). The coating solution was aspirated and tubes were blocked by adding 3% Karion FP, 0.5% bovine serum albumin and incubation for one hour. The blocking solution was discarded. The peptides listed in table 2 were dissolved in 300 mmol/L potassiumphosphate, 100 mmol/L NaCl, 10 mmol/L Na-EDTA, 0.5% bovine serum albumin; 20 tabs/L Complete Protease Inhibitor Cocktail Tablets (Roche AG);, pH 7.0) at a concentration of 10 ng/0.3 mL each, and 0.3 mL per peptide solution were pipetted per streptavidin tube. Peptides solutions were incubated in the tubes for two hours at 22° C. under agitation and washed two times with PBS buffer, pH 7.4.

Binding Assay:

Labeled CT-H antibody was diluted in (300 mmol/L potassiumphosphate, 100 mmol/L NaCl, 10 mmol/L Na-EDTA, 5 g/L Bovine Serum Albumin, pH 7.0). The final concentration was approx. 800.000 relative light units (RLU) of labelled antibody (approx. 20 ng labeled antibody) per 300 µL. Of this solution 300 µL were pipetted in each peptide/streptavidin tube and incubated tubes for two hours at 22° C. under agitation Unbound tracer was removed by washing 5 times (each 1 ml) with washing solution (20 mM PBS, pH 7.4, 0.1% Triton X-100). Tube-bound chemiluminescence was measured by using the LB 953 Luminometer (Berthold). Binding of CT-H to each peptide was expressed as percentage of binding observed in comparison to binding obtained against peptide P 33-52 NH2 (table 2).

It is evident from table 2 that the CT-H antibody very specifically binds to peptide P 33-52 NH2. Virtually no binding was detected against the same peptide, when the C-terminal amide function was replaced by a carboxyl group (P 33-52 COOH). Similarily, virtually no binding was observed when either a longer peptide or shorter peptides were tested. These results clearly demonstrate that antibody CT-H specifically binds to the C-terminal region of ADM and requires a free amidated tyrosine residue (position 52 in ADM) for binding.

Besides the CT-H antibody, additional antibodies were generated by the same immunization procedure as used for CT-H and selected by their ability to bind peptide APR-SKISPQGY-NH2 (SEQ ID NO: 1). Their epitope specificity was determined in the same way as described above for the CT-H antibody. Binding of the antibodies to each peptide was expressed as percentage of binding observed in comparison to binding obtained against peptide P 33-52 NH2 (table 3).

TABLE 3

Epitop Mapping of various monoclonal antibodies: Adrenomedulhn-related peptides are shown. Binding of each antibody to each peptide is expressed as percentage of binding observed in comparison to binding obtained against peptide P 33-52 NH2. Table 3 demonstrates that monoclonal anti-Adrenomedullin antibodies can be obtained with different epitope specificities

| Peptide # | Amino acid sequence | Position within ADM | Binding of CT-H [Bx/B P 33-52 NH2] | Binding of CT-H-1 [Bx/B P 33-52 NH2] | Binding of CT-H-2 [Bx/B P 33-52 NH2] | Binding of CT-H-Gly [Bx/B P 33-52 NH2] | Binding of CT-H-OH [Bx/B P 33-52 NH2] | Binding of CT-H-3 [Bx/B P 33-52 NH2] |
|---|---|---|---|---|---|---|---|---|
| P 33-52 + G | Biotin-FTDKDKDNVAPRSKISPQGYG-OH | 33-52 + G | 0.09% | 0.04% | 0.03% | 427.66% | 357.01% | 0.03% |
| P 33-52 COOH | Biotin-FTDKDKDNVAPRSKISPQGY-OH | 33-52 | 0.03% | 0.03% | 0.03% | 0.06% | 2846.67% | 0.03% |
| P 33-52 NH2 | Biotin-FTDKDKDNVAPRSKISPQGY-NH2 | 33-52 | 100.00% | 100.00% | 100.00% | 100.00% | 100.00% | 100.00% |
| P 33-51 | Biotin-FTDKDKDNVAPRSKISPQG-OH | 33-51 | 0.02% | 0.05% | 0.03% | 0.06% | 10.16% | 0.02% |
| P 33-50 | Biotin-FTDKDKDNVAPRSKISPQ-OH | 33-50 | 0.02% | 0.04% | 0.02% | 0.05% | 10.16% | 0.00% |
| P 33-49 | Biotin-FTDKDKDNVAPRSKISP-OH | 33-49 | 0.02% | 0.04% | 0.03% | 0.04% | 9.37% | 0.03% |
| P 33-48 | Biotin-FTDKDKDNVAPRSKIS-OH | 33-48 | 0.02% | 0.03% | 0.07% | 0.04% | 11.73% | 0.03% |
| P 33-47 | Biotin-FTDKDKDNVAPRSKI-OH | 33-47 | 0.02% | 0.04% | 0.05% | 0.05% | 13.31% | 0.03% |
| P 33-46 | Biotin-FTDKDKDNVAPRSK-OH | 33-46 | 0.02% | 0.03% | 0.03% | 0.05% | 9.37% | 0.03% |

Example 2

Xenograft Breast Tumor Model

Monolayer MDA-MB-231 cells (CPQ-82, ProQinase), a well-established breast cancer cell line, were grown in DMEM+10% FCS. The cells were cultured in a humidified atmosphere of 90% air and 10% carbon dioxide at 37° C. Media was routinely changed every 3 days. Confluent cultures were split 1:3 every 3-4 days using Trypsin/EDTA and seeded at a density of approximately 3-4×10$^6$ cells/15 cm$^2$ + 25 mL medium.

Female BALB/c nude (CAnN.Cg-Foxn1$^{nu}$/Crl) Mice (Charles River GmbH, Sulzfeld, Germany) aged 4-5 weeks at delivery and weighing approximately 15-18 g were kept under optimum hygienic conditions, air-conditioned with 10-15 air changes per hour, and continually monitored environment with target ranges for temperature 22±3° C. and for relative humidity 30-70%, 12 hours artificial fluorescent light/12 hours dark. Maximum 4 animals were kept per individual ventilated cage (IVC) and fed with a diet consisting of M-Zucht (ssniff Spezialdiäten GmbH) and autoclaved community tab water.

After an acclimatization period of 5 days (day 0), 5×10$^6$ MDA-MB-231 in 100 µL PBS buffer were implanted subcutaneously into the left flank of the female BALB/c nude mice using a 29 G needle syringe. In the following, animal weights were measured (balance: Mettler Toledo PB602-L). Primary tumour volumes were measured by callipering (manual calliper, OMC Fontana). Tumour volumes were calculated according to the formula W$^2$×L/2 (L=length and W=the perpendicular width of the tumour, L>W). After 40 days a mean tumour volume of approximately 150 mm$^3$ was reached and tumour-bearing animals were randomised into 4 groups. On the following day (day 41), administration of anti-adrenomedullin antibodies and an unspecific mouse-IgG as control (table 4) was started.

The antibodies were administered intravenously (i.v.) on a bi-daily schedule. Antibodies were dissolved in a PBS buffer and sterile filtered prior to application.

TABLE 4

Overview of antibodies investigated in the xenograft model

| Antibody used for treatment | Target sequence | Conc. | Route | Scheme | Matrix | Animals treated |
|---|---|---|---|---|---|---|
| CT-H | CAPRSKISPQGY-NH2 (SEQ ID NO: 14) | 4 mg/kg on first day of | i.v. | 1x every 2 | PBS | 8 |

TABLE 4-continued

Overview of antibodies investigated in the xenograft model

| Antibody used for treatment | Target sequence | Conc. | Route | Scheme | Matrix | Animals treated |
|---|---|---|---|---|---|---|
| NT-H | YRQSMNNFQGLRSF GCRFGTC (SEQ ID NO: 12) | treatment, 2 mg/kg for the rest of the treatments. | | days | | 8 |
| MR-H | CTVQKLAHQIYQ (SEQ ID NO: 13) | | | | | 8 |
| Control | — | | | | | 16 |

Animal behavior and welfare was observed 5 times a week (on working days). Animal weight was measured three times a week after randomization (every Monday, Wednesday and Friday). Primary tumour growth was recorded twice weekly (Monday and Friday) after randomization by calliper measurement.

Until the end of the scheduled study period (day 56) none of the animals had died. On day 56, the study was terminated; all animals were sacrificed and a necropsy was performed.

Statistical Analysis

All data analysis was performed using GraphPad Prism 5 from GraphPad Software, Inc., San Diego, USA and IBM SPSS Statistics Standard from IBM Corp., New York, USA.

The average absolute tumour volumes per group were calculated. The tumour growth was calculated as relative changes of tumour volume on day x in comparison to tumour volume on the first day of treatment (day 41).

$$\frac{\text{Tumour volume day } x \text{ [mm}^3\text{]}}{\text{Tumour volume day 41 [mm}^3\text{]}} = \text{relative tumour growth on day } x$$

Relative tumour growth for each of the anti-adrenomedullin-antibody treated groups was compared to tumour growth in the group treated with the unspecific mouse IgG.

Results

The antibodies directed against the N-terminal and midregional moieties of Adrenomedullin showed a slight but statistically not significant effect on tumour growth (FIG. 1). The effect of the anti-midregional antibody was more pronounced than for the anti-N-terminal antibody (FIG. 1). In contrast, the antibody against the C-terminus of Adrenomedullin reduced tumour growth significantly in comparison to the control group (FIG. 1).

Detailed data are shown below: The tumour volumes for each group (those treated with NT-H, MR-H, CT-H and control antibody, respectively) are shown in the following tables 5-8:

TABLE 5

Tumour volumes [mm³] for each animal per day. Treatment with NT-H was started on day 41.

| day | 27 | 31 | 34 | 36 | 38 | 41 | 45 | 48 | 50 | 52 | 55 | 56 |
|---|---|---|---|---|---|---|---|---|---|---|---|---|
| tumour vol | 62.5 | 126 | 126 | 126 | 196 | 171.5 | 256 | 405 | 500 | 500 | 550 | 665.5 |
| tumour vol | 62.5 | 40 | 62.5 | 75 | 108 | 108 | 126 | 126 | 171.5 | 196 | 288 | 256 |
| tumour vol | 108 | 108 | 126 | 126 | 171.5 | 196 | 220.5 | 320 | 320 | 445.5 | 526.5 | 526.5 |
| tumour vol | 62.5 | 62.5 | 62.5 | 75 | 75 | 126 | 171.5 | 171.5 | 171.5 | 256 | 288 | 288 |
| tumour vol | 75 | 108 | 126 | 196 | 196 | 288 | 445.5 | 600 | 650 | 1372 | 1080 | 1080 |
| tumour vol | 62.5 | 75 | 87.5 | 126 | 144 | 196 | 196 | 320 | 320 | 445.5 | 352 | 445.5 |
| tumour vol | 62.5 | 40 | 75 | 62.5 | 75 | 75 | 108 | 126 | 196 | 288 | 288 | 288 |
| tumour vol | 62.5 | 108 | 108 | 108 | 126 | 144 | 196 | 196 | 196 | 220.5 | 320 | 405 |

TABLE 6

Tumour volumes [mm³] for each animal per day. Treatment with MR-H was started on day 41.

| day | 27 | 31 | 34 | 36 | 38 | 41 | 45 | 48 | 50 | 52 | 55 | 56 |
|---|---|---|---|---|---|---|---|---|---|---|---|---|
| tumour vol | 64.5 | 128 | 129 | 129 | 187 | 173 | 253 | 398 | 505 | 510 | 570 | 690 |
| tumour vol | 61.3 | 42 | 64 | 80 | 110 | 111 | 128 | 130 | 168 | 180 | 260 | 260 |
| tumour vol | 110 | 111 | 128 | 129 | 173 | 200 | 219 | 310 | 311 | 430 | 510 | 511 |
| tumour vol | 63 | 64 | 65 | 73 | 75 | 120 | 168 | 169 | 170 | 248 | 280 | 281 |
| tumour vol | 74 | 111 | 125 | 188 | 192 | 290 | 420 | 580 | 612 | 1250 | 1080 | 1080 |
| tumour vol | 61 | 73 | 85 | 123 | 140 | 187 | 192 | 300 | 301 | 413 | 341 | 420 |
| tumour vol | 64 | 45 | 74 | 65 | 75 | 76 | 107 | 124 | 190 | 276 | 278 | 280 |
| tumour vol | 62 | 100 | 102 | 106 | 125 | 143 | 187 | 190 | 192 | 215 | 310 | 395 |

TABLE 7

Tumour volumes [mm³] for each animal per day. Treatment with CT-H was started on day 41.

| day | 31 | 34 | 36 | 38 | 41 | 45 | 48 | 50 | 52 | 55 | 56 |
|---|---|---|---|---|---|---|---|---|---|---|---|
| tumour vol | 75 | 108 | 108 | 108 | 171.5 | 196 | 256 | 405 | 500 | 550 | 726 |
| tumour vol | 75 | 87.5 | 126 | 144 | 220.5 | 320 | 405 | 550 | 600 | 786.5 | 786.5 |
| tumour vol | 196 | 196 | 196 | 196 | 220.5 | 320 | 405 | 405 | 445.5 | 550 | 600 |
| tumour vol | 62.5 | 62.5 | 62.5 | 62.5 | 126 | 62.5 | 62.5 | 62.5 | 108 | 62.5 | 62.5 |
| tumour vol | 62.5 | 62.5 | 62.5 | 75 | 108 | 126 | 87.5 | 126 | 144 | 171.5 | 196 |
| tumour vol | 108 | 108 | 75 | 108 | 126 | 171.5 | 171.5 | 171.5 | 256 | 256 | 256 |
| tumour vol | 62.5 | 108 | 108 | 108 | 171.5 | 256 | 288 | 288 | 405 | 500 | 550 |
| tumour vol | 32 | 62.5 | 40 | 40 | 75 | 126 | 87.5 | 87.5 | 144 | 126 | 144 |

TABLE 8

Tumour volumes [mm³] for each animal per day. Treatment with control antibody was started on day 41.

| day | 27 | 31 | 34 | 36 | 38 | 41 | 45 | 48 | 50 | 52 | 55 | 56 |
|---|---|---|---|---|---|---|---|---|---|---|---|---|
| tumour vol | 32 | 62.5 | 62.5 | 75 | 108 | 126 | 126 | 196 | 196 | 256 | 288 | 405 |
| tumour vol | 75 | 75 | 108 | 108 | 171.5 | 196 | 288 | 364.5 | 288 | 500 | 600 | 726 |
| tumour vol | 13.5 | 13.5 | 32 | 32 | 32 | 62.5 | 108 | 75 | 108 | 171.5 | 171.5 | 196 |
| tumour vol | 40 | 75 | 75 | 75 | 75 | 87.5 | 126 | 196 | 196 | 220.5 | 288 | 320 |
| tumour vol | 62.5 | 75 | 75 | 108 | 126 | 171.5 | 220.5 | 288 | 288 | 405 | 445.5 | 600 |
| tumour vol | 62.5 | 108 | 126 | 126 | 196 | 288 | 445.5 | 726 | 600 | 786.5 | 1008 | 1183 |
| tumour vol | 62.5 | 75 | 75 | 75 | 75 | 126 | 196 | 196 | 220.5 | 405 | 320 | 445.5 |
| tumour vol | 75 | 75 | 87.5 | 126 | 126 | 196 | 288 | 445.5 | 445.5 | 550 | 550 | 700 |
| tumour vol | 32 | 62.5 | 62.5 | 108 | 126 | 144 | 288 | 405 | 405 | 405 | 550 | 726 |
| tumour vol | 108 | 108 | 108 | 108 | 126 | 171.5 | 220.5 | 220.5 | 288 | 288 | 405 | 550 |
| tumour vol | 62.5 | 75 | 126 | 171.5 | 171.5 | 256 | 500 | 500 | 500 | 665.5 | 864 | 936 |
| tumour vol | 75 | 75 | 75 | 87.5 | 87.5 | 196 | 196 | 320 | 320 | 320 | 405 | 445.5 |
| tumour vol | 62.5 | 75 | 75 | 75 | 75 | 87.5 | 196 | 171.5 | 196 | 288 | 220.5 | 288 |
| tumour vol | 32 | 32 | 62.5 | 32 | 32 | 62.5 | 62.5 | 75 | 108 | 108 | 108 | 108 |
| tumour vol | 32 | 62.5 | 108 | 108 | 108 | 171.5 | 220.5 | 320 | 405 | 445.5 | 726 | 726 |

LITERATURE LIST

1. Ishikawa T, Chen J, Wang J, Okada F, Sugiyama T, Kobayashi T, Shindo M, Higashino F, Katoh H, Asaka M et al: Adrenomedullin antagonist suppresses in vivo growth of human pancreatic cancer cells in SCID mice by suppressing angiogenesis. *Oncogene* 2003, 22(8):1238-1242.
2. Fang C, Miguel M A, Avis I, Martinez A, Zudaire E, Cuttitta F: Non-peptide small molecule regulators of lymphangiogenesis. *Lymphatic research and biology* 2009, 7(4):189-196.
3. Kaafarani I, Fernandez-Sauze S, Berenguer C, Chinot O, Delfino C, Dussert C, Metellus P, Boudouresque F, Mabrouk K, Grisoli F et al: Targeting adrenomedullin receptors with systemic delivery of neutralizing antibodies inhibits tumor angiogenesis and suppresses growth of human tumor xenografts in mice. *FASEB journal: official publication of the Federation of American Societies for Experimental Biology* 2009, 23(10):3424-3435.
4. Nouguerede E, Berenguer C, Garcia S, Bennani B, Delfino C, Nanni I, Dahan L, Gasmi M, Seitz J F, Martin P M et al: Expression of adrenomedullin in human colorectal tumors and its role in cell growth and invasion in vitro and in xenograft growth in vivo. *Cancer medicine* 2013, 2(2):196-207.
5. Ouafik L, Sauze S, Boudouresque F, Chinot O, Delfino C, Fina F, Vuaroqueaux V, Dussert C, Palmari J, Dufour H et al: Neutralization of adrenomedullin inhibits the growth of human glioblastoma cell lines in vitro and suppresses tumor xenograft growth in vivo. *The American journal of pathology* 2002, 160(4):1279-1292.
6. Miller M J, Martinez A, Unsworth E J, Thiele C J, Moody T W, Elsasser T, Cuttitta F: Adrenomedullin expression in human tumor cell lines. Its potential role as an autocrine growth factor. *The Journal of biological chemistry* 1996, 271(38):23345-23351.
7. Martinez A, Weaver C, Lopez J, Bhathena S J, Elsasser T H, Miller M J, Moody T W, Unsworth E J, Cuttitta F: Regulation of insulin secretion and blood glucose metabolism by adrenomedullin *Endocrinology* 1996, 137(6): 2626-2632.
8. Nishikimi T, Kitamura K, Saito Y, Shimada K, Ishimitsu T, Takamiya M, Kangawa K, Matsuo H, Eto T, Omae T et al: Clinical studies on the sites of production and clearance of circulating adrenomedullin in human subjects. *Hypertension* 1994, 24(5):600-604.
9. Zudaire E, Martinez A, Cuttitta F: Adrenomedullin and cancer. *Regulatory peptides* 2003, 112(1-3):175-183.

BRIEF DESCRIPTION OF DRAWINGS

FIG. 1:

FIG. 1 shows the increase of tumor volume over time dependent on treatment with compounds. Compounds investigated were NT-H (monoclonal antibody raised against the N-terminal moiety of human Adrenomedullin), MR-H (monoclonal antibody raised against the midregional moiety of human Adrenomedullin), CT-H (monoclonal antibody raised against the C-terminal moiety of human Adrenomedullin) and Con (unspecific control antibody). Reduction of tumour growth was significant for CT-H (p=0.038); for NT-H and MR-H there was a trend for efficacy, but the effect was not statistically significant.

The invention claimed is:

1. A method for the treatment of cancer comprising:
   administering an effective amount of an antibody to a patient in need thereof wherein said antibody is obtained by a method comprising:
   immunizing with an antigen containing a C-terminal portion of ADM including the free C-terminal amidated tyrosine residue of ADM that is SEQ ID NO: 1: APRSKISPQGY, and
   selecting IgG antibodies which require the C-terminally amidated tyrosine residue at the C-terminal portion of ADM that is SEQ ID NO: 1: APRSKISPQGY for binding.

2. The method of claim 1 wherein said cancer is selected from the group consisting of prostate, breast, colon, lung, bladder, skin, uterus, cervix, oral cavity and pharynx, stomach, ovaries, kidney, pancreas, non-Hodgekin-lymphome, leukemia, liver, esophagus, testicle, thyroid, central nervous system, larynx, gall bladder, plasmocytome, and morbus hodgekin.

3. The method of claim 1, wherein said antibody exhibits a binding affinity to ADM of at least $10^{-7}$ M.

4. The method of claim 1, wherein said antibody is not ADM-binding-Protein-1 that is complement factor H.

5. The method of claim 1, wherein said antibody or antibody fragment or non-Ig scaffold binds to a region of at least 4 or at least 5 amino acids within the sequence of Adrenomedullin that is SEQ ID NO: 1: APRSKISPQGY.

6. The method of claim 1, to be administered in combination with another anti-cancer agent or be used as mono therapeuticum.

7. The method of claim 1, to be administered in combination with cytostatic agents, VEGF inhibitors, CD20 inhibitors, HER-2 inhibitors, CD-52 inhibitors, EGFR inhibitors or Tyrosine kinase inhibitors.

8. A pharmaceutical composition comprising an antibody obtained by a method comprising:
   immunizing with an antigen containing a C-terminal portion of ADM including the free C-terminal amidaied tyrosine residue of ADM that is SEQ ID NO: 1; APRSKISPQGY, and
   selecting IgG antibodies which require the C-terminally amidated tyrosine residue at the C-terminal portion of ADM that is SEQ ID NO: 1: APRSKISPQGY for binding.

9. The pharmaceutical composition of claim 8, in combination with cytostatic agents, VEGF inhibitors, CD20 inhibitors, HER-2 inhibitors, CD-52inhibitors, EGFR inhibitors, or Tyrosine kinase inhibitors.

10. The pharmaceutical composition of claim 8, in combination with Bevacizumab.

11. The pharmaceutical composition of claim 9, wherein said pharmaceutical composition is suitable for intravenous administration.

* * * * *

UNITED STATES PATENT AND TRADEMARK OFFICE
CERTIFICATE OF CORRECTION

PATENT NO. : 10,793,626 B2
APPLICATION NO. : 15/105712
DATED : October 6, 2020
INVENTOR(S) : Andreas Bergmann It is certified that error appears in the above-identified patent and that said Letters Patent is hereby corrected as shown below:

In the Claims

Column 29, Claim 1, Line 33:
Delete "SEQ ID NO: 1: APRSKISPQGY" and insert -- SEQ ID NO: 1: APRSKISPQGY-NH2 --, and Column 29, Claim 1, Lines 36 and 37:
Delete "SEQ ID NO: 1: APRSKISPQGY" and insert -- SEQ ID NO: 1: APRSKISPQGY-NH2 --.

Column 29, Claim 5, Line 52:
Delete "SEQ ID NO: 1: APRSKISPQGY" and insert -- SEQ ID NO: 1: APRSKISPQGY-NH2. --.

Column 30, Claim 8, Lines 36 and 37:
Delete "SEQ ID NO: 1: APRSKISPQGY" and insert -- SEQ ID NO: 1: APRSKISPQGY-NH2 --, and Column 30, Claim 8, Line 40:
Delete "SEQ ID NO: 1: APRSKISPQGY" and insert -- SEQ ID NO: 1: APRSKISPQGY-NH2 --.

Signed and Sealed this
Eighteenth Day of October, 2022

Katherine Kelly Vidal
*Director of the United States Patent and Trademark Office*